United States Patent [19]

Berne et al.

[11] Patent Number: 4,673,563
[45] Date of Patent: Jun. 16, 1987

[54] ADENOSINE IN THE TREATMENT OF SUPRAVENTRICULAR TACHYCARDIA

[75] Inventors: Robert M. Berne; Luiz Belardinelli; Rafael Rubio, all of Charlottesville, Va.

[73] Assignee: The University of Virginia Alumni Patents Foundation, Charlottesville, Va.

[21] Appl. No.: 721,122

[22] Filed: Apr. 8, 1985

Related U.S. Application Data

[63] Continuation of Ser. No. 452,014, Dec. 21, 1982, abandoned, which is a continuation-in-part of Ser. No. 196,652, Oct. 14, 1980, Pat. No. 4,364,922.

[51] Int. Cl.[4] ...................... A61K 49/00; A61K 31/70
[52] U.S. Cl. .......................................... 424/9; 514/46
[58] Field of Search .............................. 514/46; 424/9

[56]  References Cited

PUBLICATIONS

Chiba et al., Differences in Chronotropic and Dromotropic Responses of the SA and AV Nodes to Adenosine and Acetylcholine, Chem. Abs. 77:1357266 (1972).
Chiba et al., Prevention of the Negative Chronotropic Effect of Adenosine by Caffeine, Chem. Abstracts 72:20464u (1969).
Chiba et al., Absence of Chronotropic Effects of Dibutyryl Cyclic Adenosine 3', 5'-Monophosphate on the Dog SA Node, Chem. Abstracts 77:135738g (1972).
Belardinelli et al., Blockage of $Ca^{2+}$ Dependent Rat Atrail Slow Action Potentials by Adenosine and Lanthanum, Pflugers Arch. 380, pp. 19-27 (1979).
Bass et al., Cardiopulmonary Effects of Autimalarial Drugs, Chem. Abstracts 77:14092h (1972).
Hopkins, Action of ATP in the Guinea Pig Heart, Chem. Abstracts 78:131917n (1973).
Szentmiklosi et al., Effect of Adenosine on the Electrical Activity of the Heart of Intact Experimental Animals, Chem. Abstracts 92: 104396z (1980).
Rand et al., Effect of Cardiac Glycosides on the Heart Block Produced in the Guinea Pig by Adenosine and Its Derivatives, Chem. Abstracts 50: 8887e (1955).
Versprille, The Chronotropic Effect of Adenosine and Hypoxanthine Derivatives on Isolated Rat Hearts Before and After Removing the Sinsauricular Node, Chem. Abst. 65:19084g (1966).
Nott, The Possible Role of Adenosine in the Coronary Dilator Action of Some Pyrimido-Pyrimidines and Pteridines, Br. J. Pharmac. 39:287-295 (1970).
Schrader et al., Adenosine as Inhibitor of Myocardial Effects of Catecholamines, Pflugers Arch. 372, pp. 29-35 (1977).
Buckley et al., Inotropic Effects of Purines and Pyrimidines on the Isolated Heart, Circulation Research 9, pp. 242-249 (1961).
Wedd et al., The Action on Cardiac Musculature and the Vagomimetic Behavior of Adenosine, J. Pharmacol 47, pp. 365-375 (1933).
Drury et al., The Physiological Activity of Adenine Compounds with Especial Reference to Their Action Upon the Mammalian Heart, J. Physiology 68, pp. 214-237 (1929).
Blakiston's New Gould Medical Dictionary, Blakiston Div., McGraw-Hill Book Co., Inc.—New York, Toronto, London, 1956 (Second Edition).
Cardiac Arrhythmias: Electrophysiology, Diagnosis & Management, Onkar S. Narula, M.D. F.A.C.C.—Williams & Wilkins, Baltimore/London, pp. 382-396.
An Introduction to Electrocardiography, L. Schamroth (Fifth Edition) Blackwell Scientific Publications-Oxford, London, Edinburgh, Melbourne, pp. 124, 125 and 195-200.
DiMarco et al., Adenosine: Electrophysiologic Effects and Therapeutic use for Terminating Paroxysmal Supraventricular Tachycardia, Circulation 68:1254 (1983).

(List continued on next page.)

*Primary Examiner*—Ethel G. Love
*Attorney, Agent, or Firm*—Oblon, Fisher, Spivak, McClelland & Maier

[57]  ABSTRACT

A method of diagnosing and treating arrhythmias caused by re-entry in the A-V node by administering to a human or animal an effective amount of adenosine that restores normal sinus rhythm.

10 Claims, 14 Drawing Figures

PUBLICATIONS

Belhassen et al., Electrophysiologic Effects of Adenosine Triphosphate and Adenosine on the Mammalian Heart: Clinical and Experimental Aspects, J. Am Coll Cardiol 4(2): 414–424 (1984).

Senges, Effect of Hypoxia on the Sinoatrial Node, Atrium, and Atrioventricular Node in the Rabbit Heart, Circ. Res. 44:856–863 (1979).

Bagdonas, Effects of Ischemia and Hypoxia on the Specialized Conducting System of the Canine Heart, Am. Heart J. 61:206–218 (1961).

Carmeliet et al., Comparative Effects of Lignocaine and Lorcainide on Conduction in the Langendorff–Perfused Guinea-Pig Heart, Cardiovasc, Res. 13:439–449 (1979).

Belardinelli, Effects of Adenosine and Adenine Nucleotides on the Atrioventricular Node of Isolated Guinea Pig Hearts, Circulation 70 (60): 1083–1091 (1984).

Belardinelli et al., Dromotropic Effects of Adenosine and Adenosine Antagonists in the Treatment of Cardiac Arrhythmias Involving the Atrioventricular Node, Pflugers Archiv. '380 Jun. 7, 1984.

Zumino et al., Effect of Ischemia and Low-Sodim Medium on Artioventricular Conduction, Am. J. Physiol. 218, 1489–1494 (1970).

Greco et al., Treatment of Paroxysmal Supraventricular Tachycardia in Infancy with Digitalis, Adenosine-5'-Triphosphate, and Verapamil: A Comparative Study, Circulation 66:504 (1982).

Puech et al., Nouv. Pres. Med. 1;606 (1972).

Motte et al., L'Adenosine Triphosphorique dans les Tachycardies Paroxystiques, Nouv. Press. Med. 1:3057–3061 (1972).

Honey et al., The Action of Adenosine Upon the Human Heart, Q. J. Med. 23:485–489 (1930).

Jezer et al., The Effect of Adenosine on Cardiac Irregularities in Man, Am. Heart. J. 9:252–258 (1933).

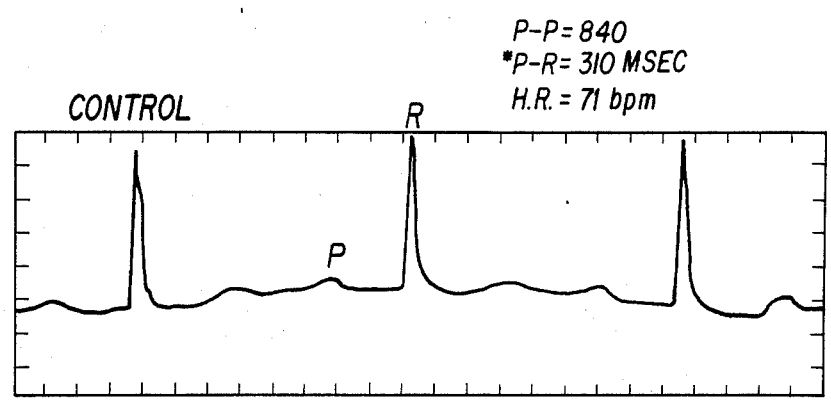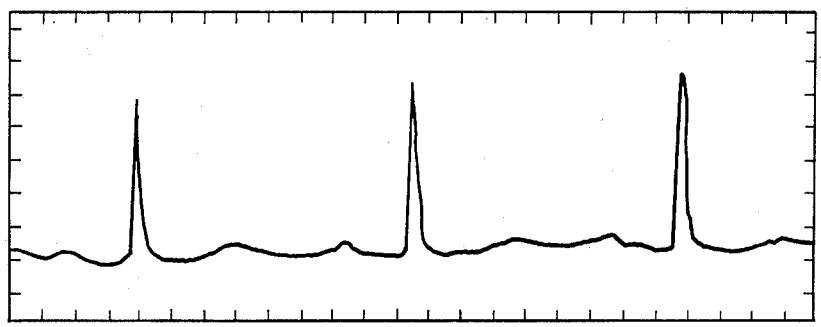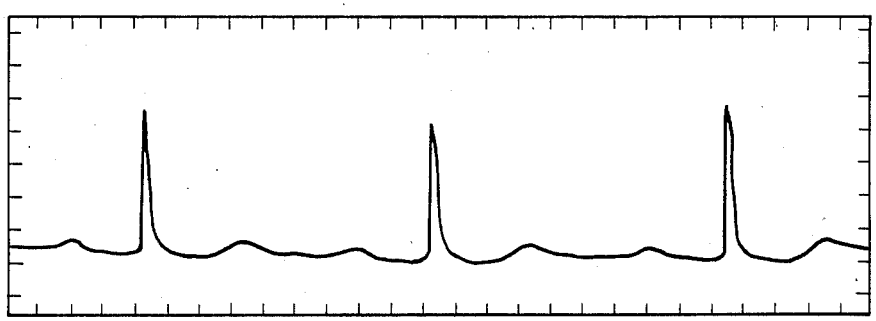
FIG. 8

PATIENT (R.G.)
CONTROL                      2nd DEGREE A-V BLOCK
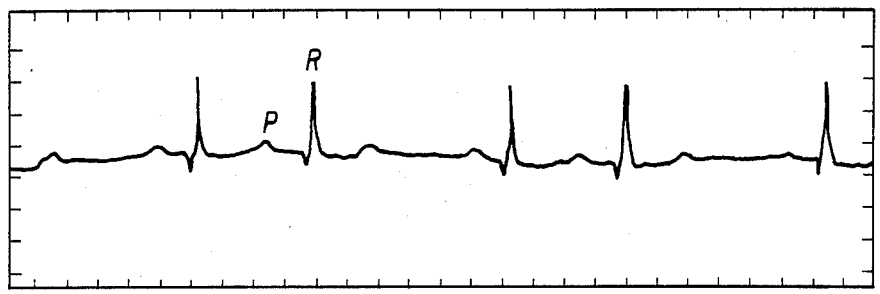
15 MIN. AMINOPHYLLINE (3mg/Kg IV.)
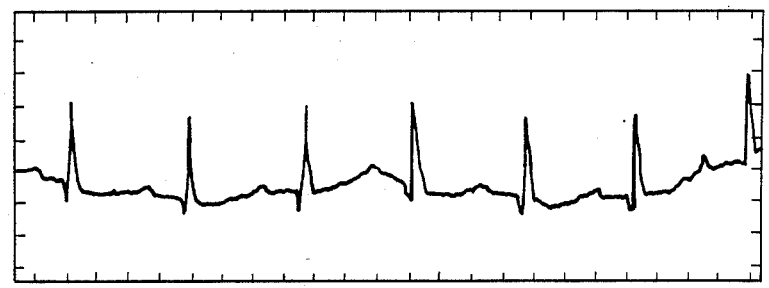
2 HRS. AMINOPHYLLINE
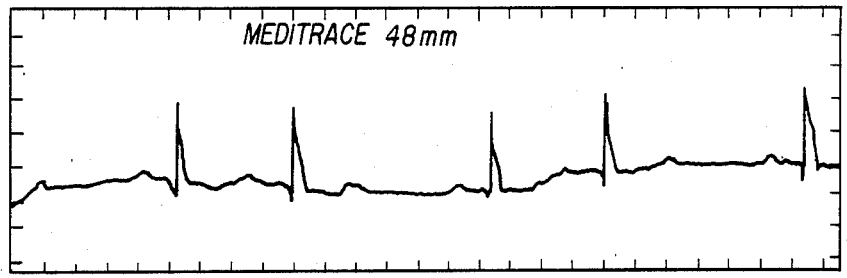
FIG. 9

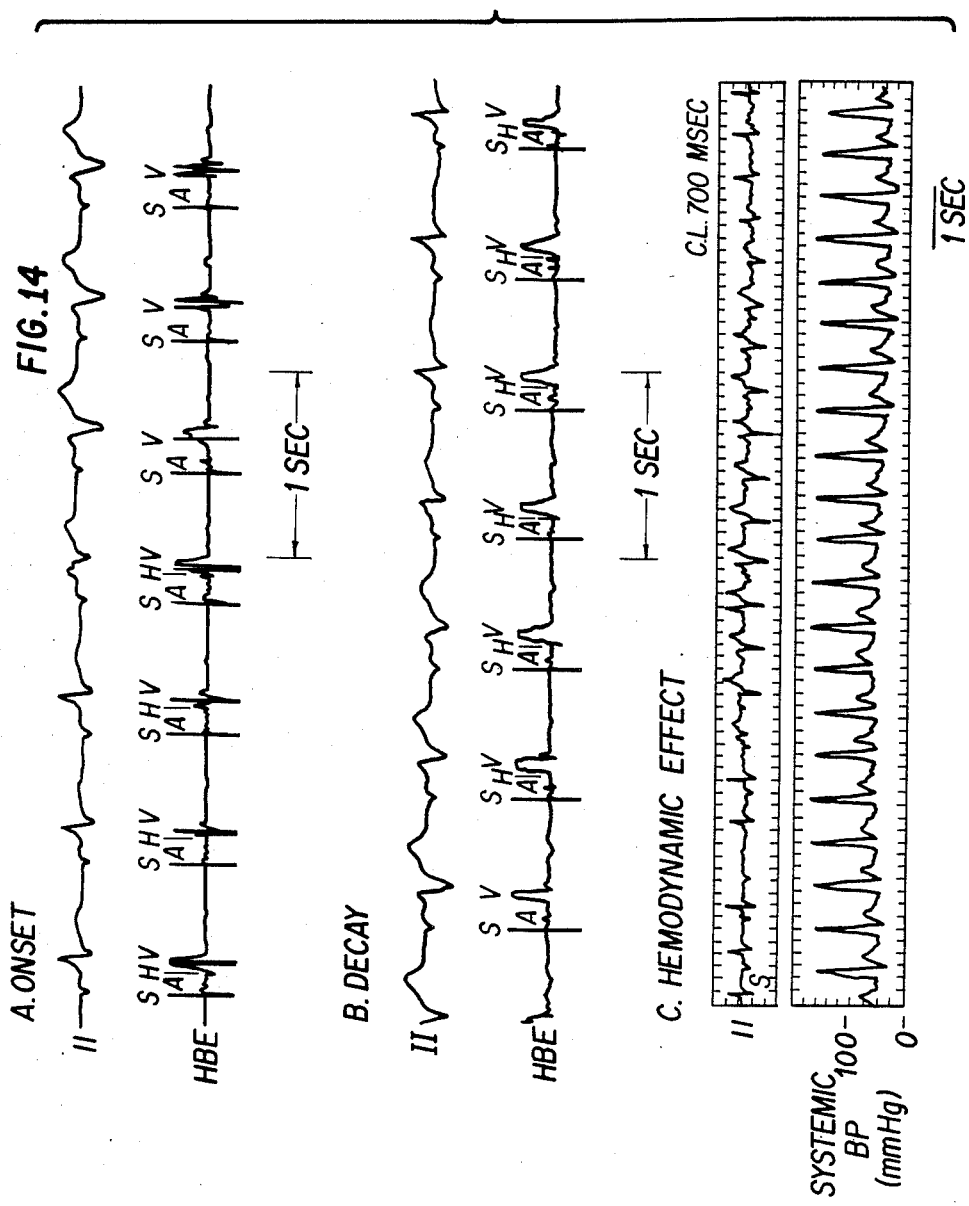

ADENOSINE IN THE TREATMENT OF SUPRAVENTRICULAR TACHYCARDIA

This application is a continuation of application Ser. No. 452,014, abandoned, filed Dec. 21,1982, which is a continuation-in-part of application Ser. No. 196,652, filed Oct. 14, 1980, now U.S. Pat. No. 4,364,922.

BACKGROUND OF THE INVENTION

1. Field of the Invention

The present invention relates to methods for treatment of supraventricular tachycardia and other arrhythmias caused by re-entry in the A-V node.

2. Description of the Prior Art

In the mammalian heart the electrical component of each heart beat originates in the sinoatrial node (pacemaker) of the heart and must pass through the atrioventricular (A-V) node in order to reach the ventricles and elicit the contraction needed to pump blood. The electrical components of a heart beat can be detected by an electrocardiogram (EKG) and appear as follows: first, an electrical impulse known as P-wave, which indicates the triggering of the sinoatrial node and activation of the atria, and second, a complex group of electrical impluses individually named Q-, R-, S-, and T-waves and collectively known as the ventricular complex, which indicates that the signal has passed the A-V node and that the ventricles are activated to contract. The Q-wave is sometimes quite small and may not be visible; therefore, the interval between atrial and ventricular depolarization (activation) is generally measured by the P-R interval. An EKG of a normal heart is shown in FIG. 1. Normally, both the interval between two P-waves (the time of a complete heart beat) and the interval between a P-wave and following R-wave are consistent from one heart beat to another. The normal P-R interval is about 0.2 second.

Various disfunctions of the heart lead to altered beating. One such alteration is heart block, which occurs when the transmission of a signal through the A-V node is impaired. Heart block leads initially to a slowing of heart beat and can progress to such a degree that beats are missed entirely or even that the atria and ventricles beat independently. Conversely, other conditions may lead to more rapid heart beat, for example, arrhythmias caused by re-entry in the A-V node. Conditions of excessively rapid heart beat are known as tachycardia. When tachycardia is caused by rapid discharges from an abnormal atrial pacemaker, it is known as paroxysmal atrial tachycardia or more recently by the name paroxysmal supraventricular tachycardia. Recent evidence suggests that many instances of paroxysmal supraventricular tachycardia are symptoms of reciprocating rhythms resulting from a short-circuit in which electrical impulses pass back through the A-V node, or more likely through an accessory pathway (e.g., Wolf-Parkinson-White, preexcitation syndrome), and initiate new beats before they would normally occur. Tachycardia usually appears in youth and often reoccurs throughout adult life, notably in individuals with preexcitation syndrome. Although paroxysmal atrial tachycardia is generally benign, the attack may ocassionally bring on congestive failure or myocardial ischemia.

Considerable information is known regarding conditions of the heart which affect A-V node transmission. These conditions include ischemia (lower blood flow to heart tissue) and hypoxia (low oxygen blood level) of the A-V node. Furthermore, it was known that A-V node action potentials (electrical potential during activity of the node) are depressed by hypoxia and, concomitantly, the atria-to-His bundle conduction time is markedly increased. The His bundle is a small bundle of atypical cardiac muscle fibers that propagates the electrical signal from the atrial to the ventricular end of the A-V node. Additionally, stimulation of the vagus nerve, the parasympathetic nerve that controls heart beat, results in slowing the heart beat and an increase in the P-R interval. The vagus nerve interacts with the heart by releasing acetylcholine, and, therefore, the presence of high levels of acetylcholine will also cause A-V conduction disturbances. Lastly, as early as 1929 it was observed that adenosine, if injected in large amounts, can produce heart block. Adenosine is normally present in myocardial tissue, as well as in other tissues, but is normally present only in much lower concentrations than those that produce heart block. Adenosine and adenine nucleotides have been shown to produce dose-dependent A-V conduction block in guinea pig hearts. Adenosine is also known to depress $Ca^{2+}$-mediated action potentials in mammalian atria.

Presently, A-V node block and specific types of tachycardia can be determined with certainty only from an electrocardiogram (EKG). If an EKG is not available, clinical techniques of heart beat monitoring by stethoscope or by taking of the pulse may give some indication of these disorders, but with considerable less certainty.

Supraventricular tachycardia is typically treated by the avoidance of factors, such as anxiety, digestive disturbances, or hyploglycemic episodes, where these factors are known to trigger episodes. Various drugs, such as digitalis and verapamil, also effective. The use of adenosine triphosphate (ATP) in order to stop paroxysmal supraventricular tachycardias and to facilitate the diagnosis of atrial tachycardia (flutter and fibrillation) by the transient A-V node block produced by this drug was introduced in 1955 [Komor et al, Lancet, 269, 93 (1955); Somlo, Lancet, 268, 1125 (1955)]. ATP was thought by its users to slow the ventricle through an independent effect that did not depend on the formation of adenosine. ATP was typically administered at a dosage rate of 30 mg. Although this dose does not usually cause major problems, a reduction in the amount of medication used is desirable, as it would be for all medications.

SUMMARY OF THE INVENTION

It is therefore a primary goal of the present invention to provide a method for diagnosis and treatment of arrhythmias caused by re-entry in the A-V node or an accessory pathway.

It is a further objective of the invention to provide a treatment method specifically for paroxysmal supraventricular tachycardia.

It is an additional objective of the present invention to use a substance of known low-toxicity in the treatment of tachycardia.

These and other objectives of the invention as will hereinafter become more readily apparent have been attained by providing a method of relieving tachycardia comprising the step of administering to a human or animal afflicted with an arrhythmia caused by re-entry in the A-V node an amount of adenosine sufficient to restore normal sinus rhythm as well as by providing a method of detecting an arrhythmia caused by re-entry in the A-V node comprising the steps of administering to a human or animal afflicted with an arrhythmia an amount of adenosine sufficient to restore normal sinus rhythm if said arrhythmia is caused by re-entry in the A-V node and monitoring heart beat of said human or animal for restoration of normal sinus rhythm.

DESCRIPTION OF THE PREFERRED EMBODIMENTS

Figure 1:
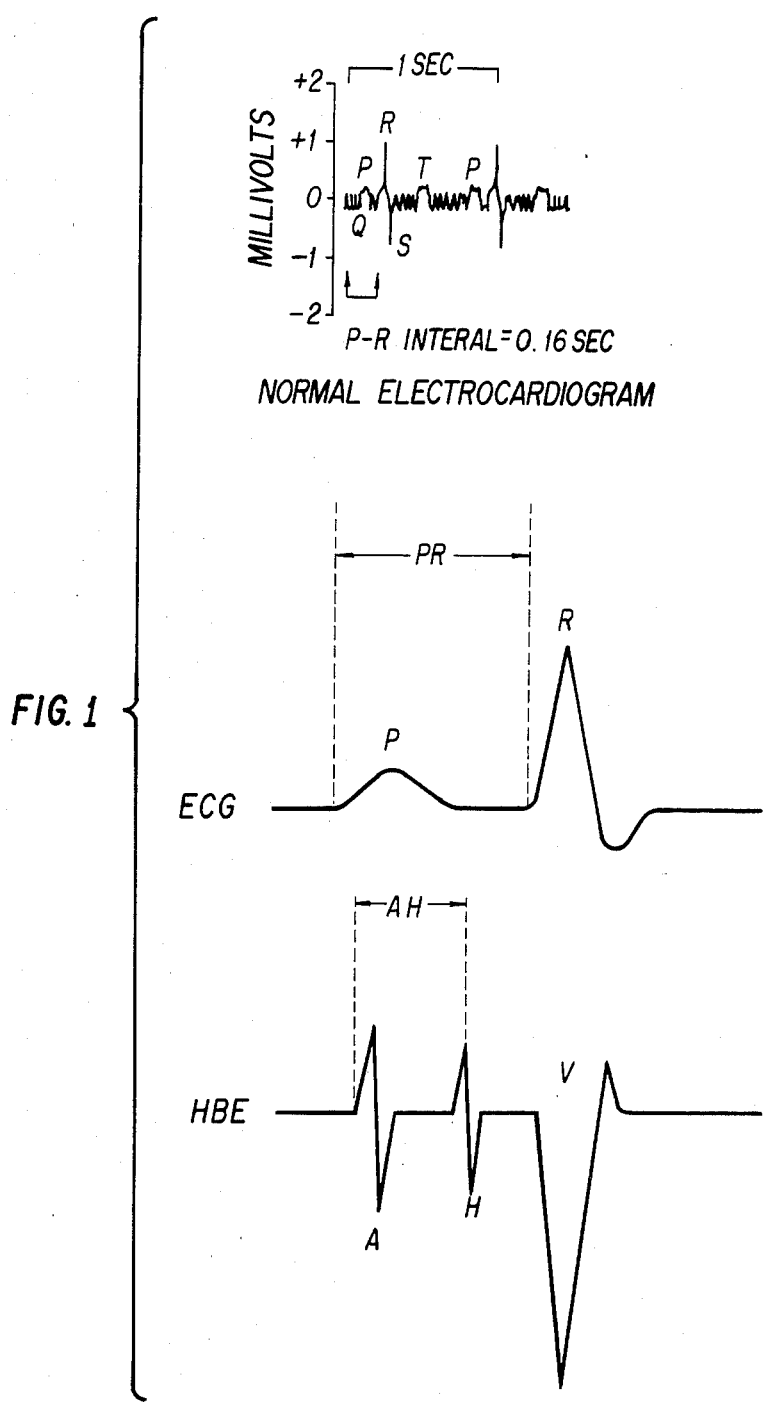

The investigations leading to the present invention are described in part in U.S. Pat. No. 4,364,922, the parent application on which this continuation-in-part is based. Prior to the disclosure in that patent of the 3-way cause-and-effect relationship of hypoxia, adenosine production, and A-V node disturbance, no rational treatment of A-V node conduction disturbances was possible. Although it was possible prior to that invention to treat A-V node disturbances by administering various drugs, no rational basis for choosing a drug was available. The novel diagnostic technique and treatment method disclosed in the patent comprises the use of an adenosine antagonist to block the action of adenosine on the A-V node. The present inventors disclosed in the original patent application that in response to hypoxia or ischemia, myocardial cells produce an excess of adenosine. This amount of adenosine is far greater than that which is present normally in myocardial tissue. The excess adenosine alters the performance of the heart muscle and blood vessels in the heart. In particular, the excessive amount of adenosine released from ischemic cells impairs A-V node conduction. Thus, the adenosine so produced is capable of slowing or interrupting the passage of the electrical impulse from the atria to the ventricles, which could lead to a slowing of heart rate and possible pump failure if excessive. The inventors showed that impairment of A-V node function by hypoxia or ischemia can be reversed or prevented by administration of antagonists of adenosine.

The present invention arose with the realization that supraventricular tachycardia and other arrhythmias caused by re-entry in the A-V node could be treated by the converse action: slowing conduction through the A-V node. However, such a use of adenosine required careful investigation before being placed into clinical practice since slowing A-V node conduction too much can result in dangerous, higher degrees of heart block (second and third degree) which reduce the efficiency of the heart beat. It has now been established through human clinical testing that the effects of adenosine on A-V conduction are dose dependent and are due to increased conduction delay between the atria and His-bundle; i.e., an increase in the A-H interval of the His-bundle electrogram. In contrast, His-bundle to ventricle (H-V interval) conduction is not altered by adenosine, even at high concentrations. Thus, the selective action of adenosine upon the A-H interval resembles other calcium channel blockers, such as verapamil and $MnCl_2$. Moreover, the A-V block caused by adenosine is accompanied by inhibition or blockade of the "slow" $Ca^{2+}$-$Na^+$-mediated action potentials in the A-V node cells, a finding consistent with adenosine depression of $Ca^{2+}$-mediated action potentials in mammalian atria and with the fact that the proximal A-V junction is more sensitive to drugs that interfere with slow $Ca^{2+}$-$Na^+$ inward current than is the distal portion. These results indicate that adenosine is safe for human use and that its dosage can be selected by the clinician who is administering the drug (for treatment or diagnosis) merely by monitoring heart rate and the effects of adenosine thereon.

Recently, it has been postulated by others that ATP released from ischemic cells was responsible for the metabolic mediation of early ischemic A-V block. This hypothesis was based on the observation that ATP infused into the A-V node artery or the anterior septal artery produces complete A-V block. However, in the isolated guinea pig heart, data now available to the present inventors indicates that A-V block caused by ATP is a result of ATP degradation to adenosine. This conclusion, which resulted in the present invention, is based on four independent observations: (1) the less hydrolyzable ATP analogue, $\beta,\gamma$-methylene ATP, has essentially no effect on A-V conduction; (2) adenosine transport blockers markedly potentiate the effects of ATP; (3) aminophylline (a competitive inhibitor of adenosine) antagonizes the ATP-induced A-H prolongation; and (4) adenosine deaminase, an enzyme that specifically inactivates adenosine but not ATP, blocks the effect of ATP.

The present inventors recently demonstrated that when adenosine is injected directed into the human right coronary artery, from which the A-V node artery originates in 85 to 90% of hearts, it caused transient A-H prolongation and A-V block. Complete A-V block in these patients was accompanied by transient ventricular standstill. Similar findings have been reported with intravenous injections of ATP, which is very effective in terminating supraventricular tachycardia due to re-entry in the A-V node [Greco et al, Circulation, 66, 509 (1982)]. As discussed above, the effects of ATP have been demonstrated by the present inventors to be due to its degradation to adenosine. The mechanism whereby ATP and adenosine terminate supraventricular tachycardia can be explained by the ability of adenosine to increase A-V conduction time (A-H prolongation). Adenosine could serve as a diagnostic tool for determination of whether or not one of the limbs of the reentrant pathway during supraventricular tachycardia includes the A-V node. During adenosine-induced transient A-V block, atrial flutter or fibrillation can be unmasked on the body surface EKG recording in order to more clearly diagnose the underlying disorder. Appropriate drug or electrotherapy can then be undertaken.

Supraventricular tachycardia and other arrhythmias caused by re-entry in the A-V node can be treated or diagnosed by administering to a human or animal afflicted with such an arrhythmia an amount of adenosine sufficient to increase the P-R interval and thus restore normal sinus rhythm. Throughout this application reference to arrhythmias "caused by re-entry in the A-V node" is intended to include those involving accessory pathways; i.e., those abnormal bundles of connective tissues existing in some heart condition that function in a similar manner to the A-V node in transmitting electrical impulses, such as the Kent bundle in W-P-W syndrome. Arrhythmias caused by re-entry in the A-V node often involve these accessory pathways as well as the A-V node itself in a circular pathway whereby the original impulse is transmitted through one impulse pathway and is reflected back through another, thereby initiating a new impulse too soon and resulting in tachycardia. While an effective amount will differ depending on the individual being treated, the exact type of disorder treated, and the severity of the attack, the effective amount can easily be determined by monitoring heart rate while administering varying amounts of adenosine.

In general, the increase in the P-R interval caused by adenosine is usually accompanied by slowing of the heart rate. Effective dosages of adenosine can be readily determined by monitoring the effect of a given dose on the P-R interval of a heart beat as measured by an electrocardiogram or by monitoring the heart rate.

A single dose of 1-8 milligrams is satisfactory as an initial dose for an adult human (70 kg). The initial dose may be adjusted to give the same relative amount on a milligram per kilogram basis for individuals of other body weights. Typically, 0.01-0.25 mg per kg of body weight is preferred with about 0.06 mg/kg being most preferred as an initial dose. The amounts stated in this paragraph are particularly preferred for diagnosis. Adjustment up or down may be made by monitoring the effect of the initial dose when adenosine is being used for treatment.

Adenosine or its stable analogues can be administered by standard methods of administration, including but not limited to intravenous injection, oral ingestion via tablets, capsules, or liquids, suppository implantation, intramuscular injection, and inhalation. Any of those methods that are able to provide a plasma level effective to result in abolition of the arrhythmia are suitable for the present invention, but because the need for rapid onset of action by the antagonist in conditions of danger to heart tissue caused by impaired heart beat, intravenous injection is preferred. Intravenous administration of adenosine may consist of a single injection, a loading dose followed by continuous administration of a lower level maintenance dose, injections spaced over a period of time, continuous injection of a low level maintenance dose, or other types of administration that are suitable for the particular needs of the individual human or animal being treated. Dosages of adenosine required for specific plasma levels are easily established by those skilled in the art. For example, to achieve an adenosine plasma concentration of $1-3\times10^{-6}M$, adenosine is administered as a bolus intravenous injection of 0.075 mg/kg into the antecubital or femoral vein. Other plasma levels may be achieved by using multiples or fractions of the doses disclosed above.

Contemplated as equivalents of adenosine are analogues and derivatives thereof which bind to the adenosine receptor to a similar or higher degree to adenosine itself.

Administration of adenosine by a method in which adenosine is absorbed into the blood stream without being destroyed is preferred. Examples, not intended to be limiting, include intravenous injection of adenosine, absorption of one of its analogues by the large intestine from suppositories, absorption by the small intestine from capsules that release an adenosine analogue in the intestine after passing through the stomach, or absorption through the lungs. Methods that require adenosine to pass through the stomach may be subject to destruction of adenosine which accordingly must be either protected in a form that is not destroyed in the stomach or administered in a larger dose so that the amount reaching the blood stream is sufficient to achieve the desired effective level.

Adenosine may be admixed with any pharmaceutically acceptable carrier or carriers, such as water, ethanol, inert solids, or any other carrier customarily used for the type of administration in question.

Adenosine may be mixed with other drugs suitable for treating disorders of the heart to produce compositions of widely ranging uses. For example, a composition comprising both propranolol and adenosine may be used to treat A-V conduction block and tachycardia at the same time.

Although this invention in its preferred embodiments is primarily adressed to use in humans, veterinary use is also anticipated and is encompassed by the invention. In this regard, adenosine may be administered to reduce heart rate in, for example, dogs, cats, horses, cattle and sheep. These examples are not intended to be limiting, but are merely illustrative of veterinary use.

Having generally described the invention, a more complete understanding can be obtained by reference to certain specific examples, which are provided herein for purposes of illustration only and are not intended to be limiting unless otherwise specified.

EXAMPLE 1

The effects of exogenous adenosine on perfused rabbit and guinea pig hearts have been demonstrated. Lengthened A-V conduction (P-R interval) resulting from this conduction is competitively inhibited by the administration of aminophylline.

Experiments were carried out using isolated, perfused rabbit and guinea pig hearts. Adult rabbits of either sex (New Zealand White), weighing 6-8 kg, were anesthetized with sodium pentobarbital (25 mg/kg,iv) whereas guinea pigs of either sex (Hartley) weighing 450-700 g, were stunned by a blow to the head. The hearts were removed rapidly and rinsed with ice cold Ringer's solution. Retrograde aortic perfusion at a constant flow (Gilson pump Minipuls-2) of 3-5 ml/min per g was initiated immediately. In all experiments the non-recirculating perfusion fluid was modified Krebs-Henseleit solution (pH 7.4) with the following composition (mM): NaCl, 121.4; KCl, 4.7; $CaCl_2$ 2.5;$MgSO_4$, 1.25; $KH_2PO_4$, 1.18; $NaHCO_3$, 25; glucose, 11. The solutions were gassed with 95% $O_2$+5% $CO_2$ and the temperature was maintained at $34°\pm1°$ C.

Figure 2:
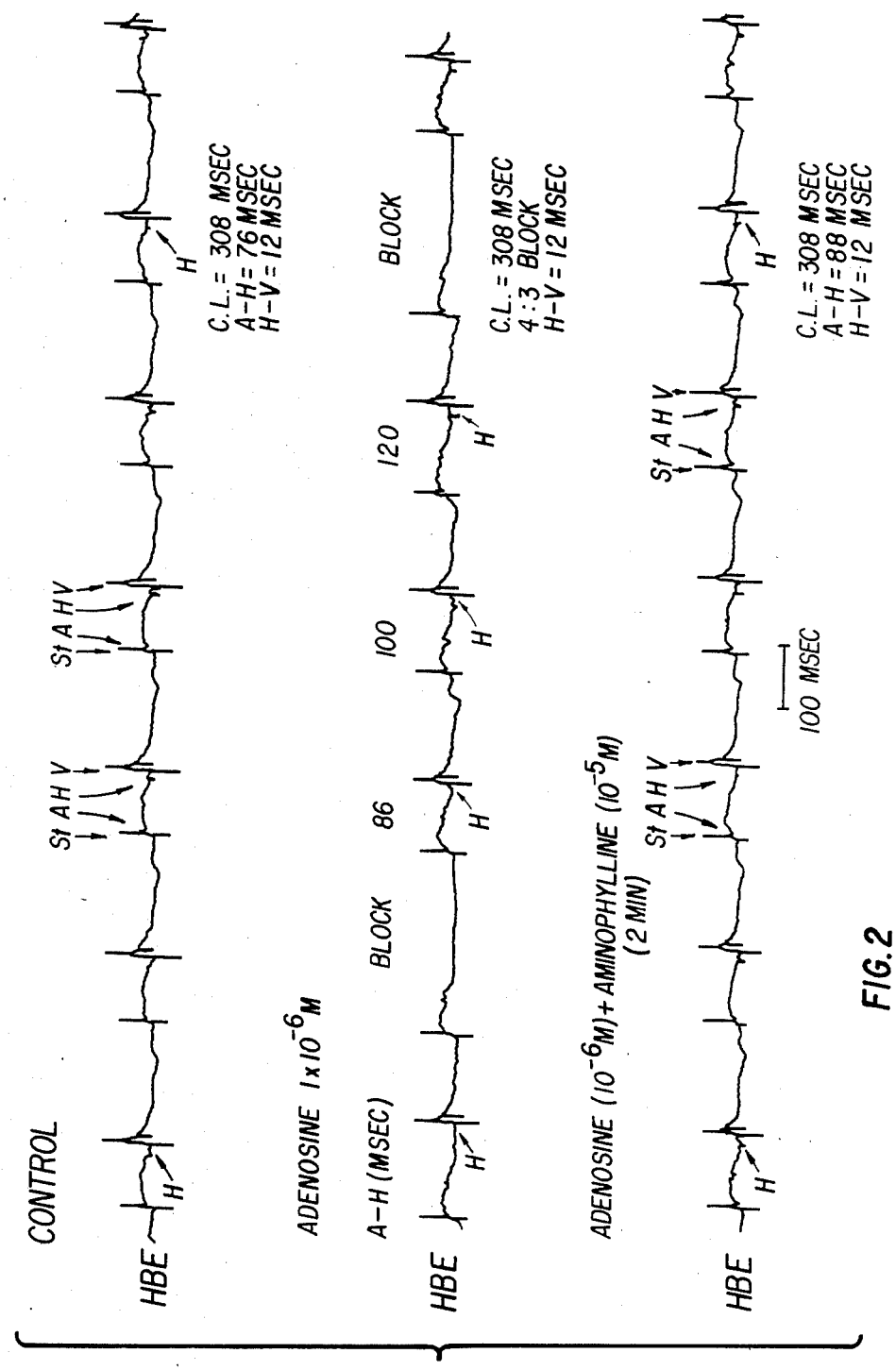
Figure 3:
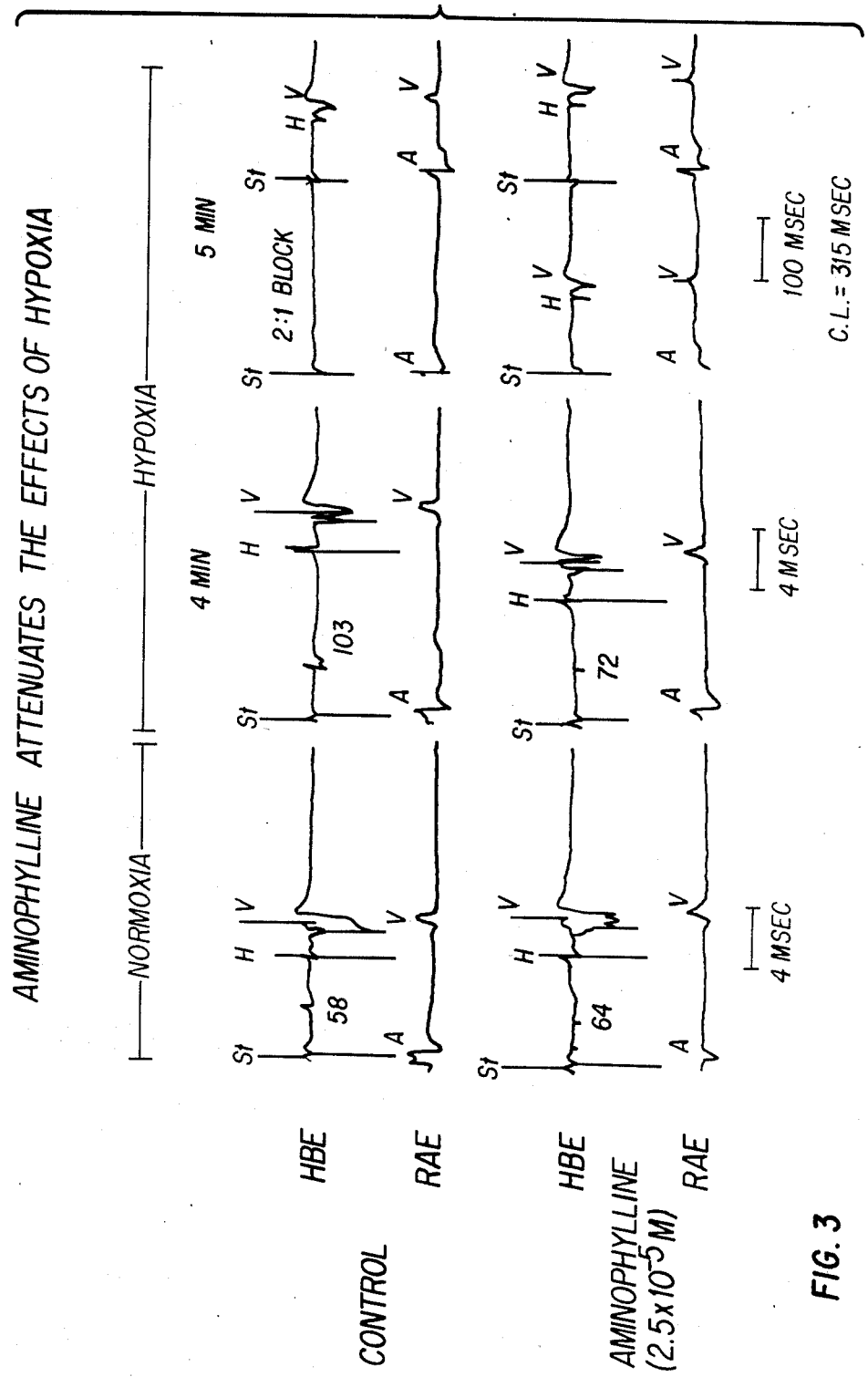

After the pericardium and other extraneous tissue had been removed, the right atrium was opened to expose the A-V node region. The sinoatrial node region also was excised. The heart was placed in a bath filled with Krebs-Henseleit solution and positioned in such a way that it was completely immersed. The right atrial wall was retracted with 6-0 nylon sutures to expose the region of the A-V node. The hearts were paced electrically at cycle lengths between 170 and 450 msec with a pair of Teflon-coated, silver wires placed on the upper surface of the right auricle. A physiological stimulator (Grass model S-48) provided the stimuli through a stimulus isolation unit as rectangular wave pulses of 2-3 msec duration and twice threshold intensity. Extracellular electrograms were recorded through bipolar, Teflon-coated, stainless steel wires (o.d., 0.0045") on the crista terminalis and left ventricle. The electrode for the His bundle electrogram (HBE) consisted of a small (2-3 mm) stainless steel electrode (insulated except for the tip) soldered to a copper wire (o.d., 0.0031"), i.e., similar to a floating electrode. These electrodes had a resistance of 2-5M$\Omega$. The position of the HBE electrode was adjusted until a discernible spike from the bundle of His was recorded (as illustrated in FIG. 2 and 3. The bipolar electrograms were obtained by connecting these two electrodes to a differential amplifier (Tektronix model 2A61). The signals from the right atrial electrogram (RAE) and HBE were amplified and displayed on a dual-beam oscilloscope (Tektronix model 502) and recorded on a strip-chart recorder (Gould-Brush model 220). Oscilloscope signals were displayed at sweep speeds of 10 to 50 msec/cm and photographed with a Kymographic camera (Grass). Strip chart recordings were obtained at a paper speed of 125 mm/sec.

On the right atrial and His bundles electrograms the stimulus artifact, the onsets of atrial (A) and ventricular (V) depolarization and the His spike (H) were identified. From these features, the following measurements were taken: (1) cycle length, defined as the interstimulus interval; (2) A-H interval which represents the conduction time from the atrial tissue to the bundle of His; (3) H-V interval, which represents the conduction time from the bundle of His to the ventricular tissue; and (4) A-V intervals, which represents the atrial to ventricular conduction time (A-VCT). The measurements are expressed in milliseconds.

After securing the electrodes 30 minutes passed before control measurements were begun. Control measurements preceded and followed all experimental interventions. When total A-V conduction time in the pre- and post-control differed by more than 10%, the intervening experimental data were discarded. Since A-V node conduction is very dependent upon cycle length, control and experimental measurements were made at similar cycle lengths. Furthermore, the effects of each experimental maneuver were observed at more than one cycle length.

Adenosine (Boehringer Mannheim or Sigma) was dissolved in perfusion medium and infused to achieve perfusion fluid concentrations of $10^{-7}$ to $10^{-4}$M. Aminophylline (Invenex), acetylcholine (Sigma), atropine (Sigma), and manganese chloride (Mallinckrodt) were also dissolved in perfusion medium and infused. To ensure complete mixing, all agents were introduced into the perfusion line, via a T-connection, before the peristaltic pump. All drug concentrations given herein are the calculated arterial perfusion fluid concentrations.

In most cases, statistical analyses were based on the t-distribution for paired (experimental vs. average pre- and post-control) data. Linear regression analysis was used to evaluate the possible dependence of the percent increment in A-V conduction time upon cardiac cycle length for various doses of adenosine. One-way anaylsis of variance was used to evaluate the dependent of responses on adenosine dose (Snedecor and Chochran, Statistical Methods, ed. 6, chap. 10, Ames, Iowa, The Iowa State University Press, pp. 258-298 (1976)).

Figure 4:
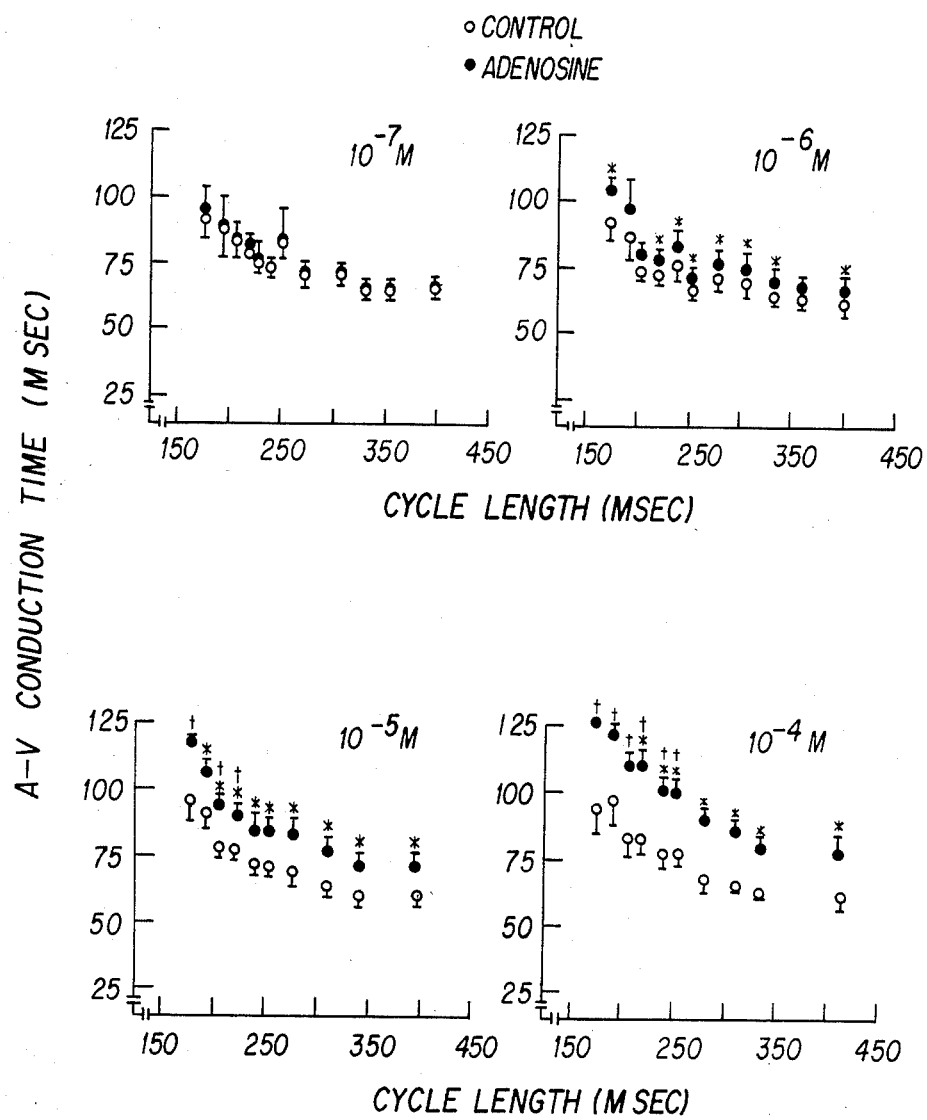
Figure 5:
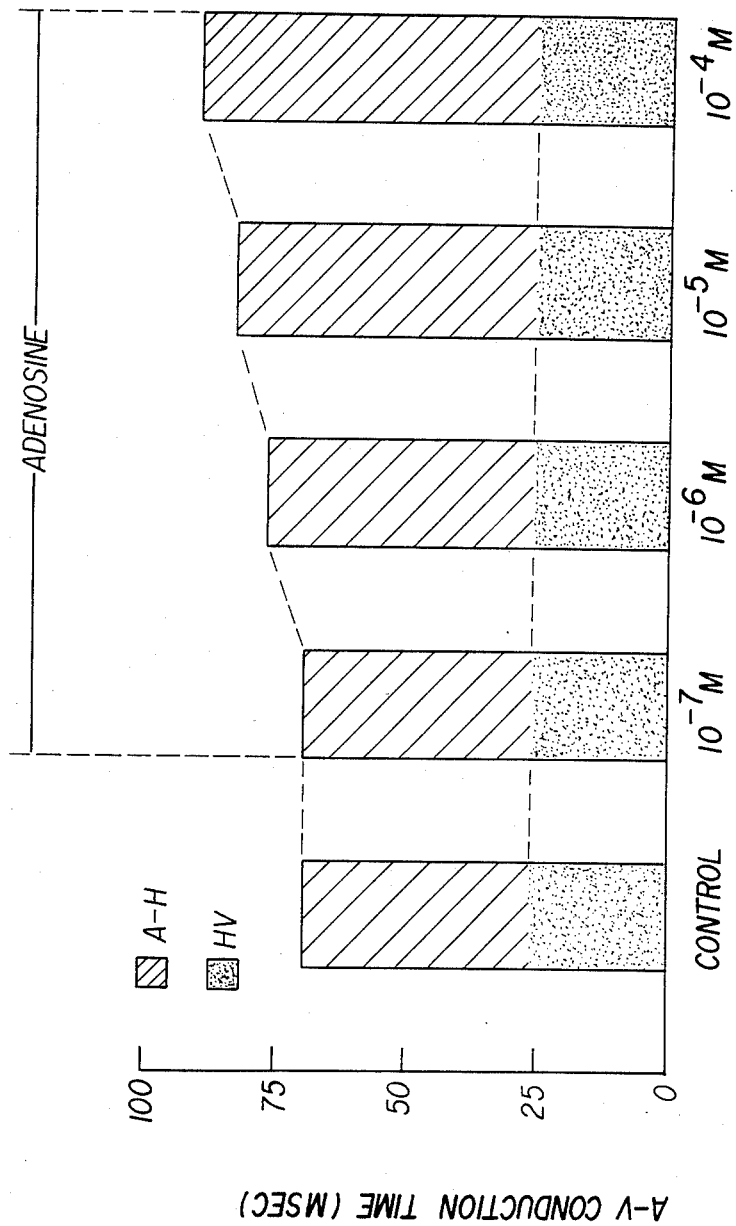

Adenosine prolonged A-V conduction time in isolated perfused rabbit hearts. In these experiments, displayed in FIGS. 4 and 5, the isolated heart preparation was paced at several different rates during a control (no infusion) period. Adenosine was then infused to achieve a perfusion fluid concentration of $10^{-7}$, $10^{-6}$, $10^{-5}$, or $10^{-4}$M and the paced rates were repeated. Finally, a post-control series of measurements was made. As seen in FIG. 5, adenosine prolonged the A-H interval without changing the H-V interval. FIG. 4 summarizes the data from 20 rabbit heart preparations. No effect of adenosine was seen at $10^{-7}$M, but the higher doses clearly prolonged the A-V conduction time. Statistically significant replicated points at certain cycle lengths were obtained. The trend of the data was clear, however, as 150 of 155 trials at the three highest doses showed prolonged A-V conduction time with adenosine. Another statistical problem was caused by the tendency of $10^{-5}$ and $10^{-4}$M adenosine to cause second-degree heart block at the higher heart rates in some preparations (11 trials indicated at crosses in FIG. 5). Although this made quantification difficult, it clearly strengthens the conclusion that adenosine prolongs A-V conduction is isolated rabbit hearts.

FIG. 4 also demonstrates the tendency for A-V conduction time to increase with heart rate, i.e., as cycle length decreases. This is a well-known effect (Merideth et al., Cir. Res., 23, pp. 69-85 (1968)). The A-V conduction time was subdivided into its A-H and H-V intervals in 14 of the 20 rabbit hearts in this series (i.e., those in which a His electrogram was obtained). The H-V interval averaged $25 \pm 1$ msec for these hearts and showed no dependence on cycle length. Therefore, all the changes in A-V conduction time as a function of cycle length are accounted for by changes in the A-H interval. In addition to showing that the adenosine-induced changes in A-V conduction time were due solely to changes in the A-H interval, FIG. 5 also indicates a significant concentrationdependence of this adenosine effect. The percentage increments in A-V conduction time showed only very weak dependence on cycle length for any adenosine dose. Linear regression analysis of these percent increment values against cycle length yielded low $R^2$ values (0.05-0.46) and shallow slopes (1-3% per 100 msec cycle length) for the groups of data for the three highest adenosine concentrations. Therefore, the values were pooled for each dose. Cases in which second-degree heart block was induced by adenosine were not included in these calculations, leading to some underestimation of the effects of the high adenosine concentrations. The lowest adenosine concentration ($10^{-7}$M) caused a $1 \pm 1\%$ (mean$\pm$SEM, $\eta=23$ paired comparisons) increase in A-V conduction time. This was not significantly different from no effect. But, adenosine at $10^{-6}$M caused an $8 \pm 1\%$ ($\eta=52$) increase in A-V conduction time; adenosine at $10^{-5}$M caused a $21 \pm 2\%$ ($\eta=59$) increase; adenosine at $10^{-4}$M caused a $31 \pm 2\%$ ($\eta=44$) increase. These values were all significantly different from zero and from each other (analysis of variance for one-way classification by adenosine dose).

Figure 6:
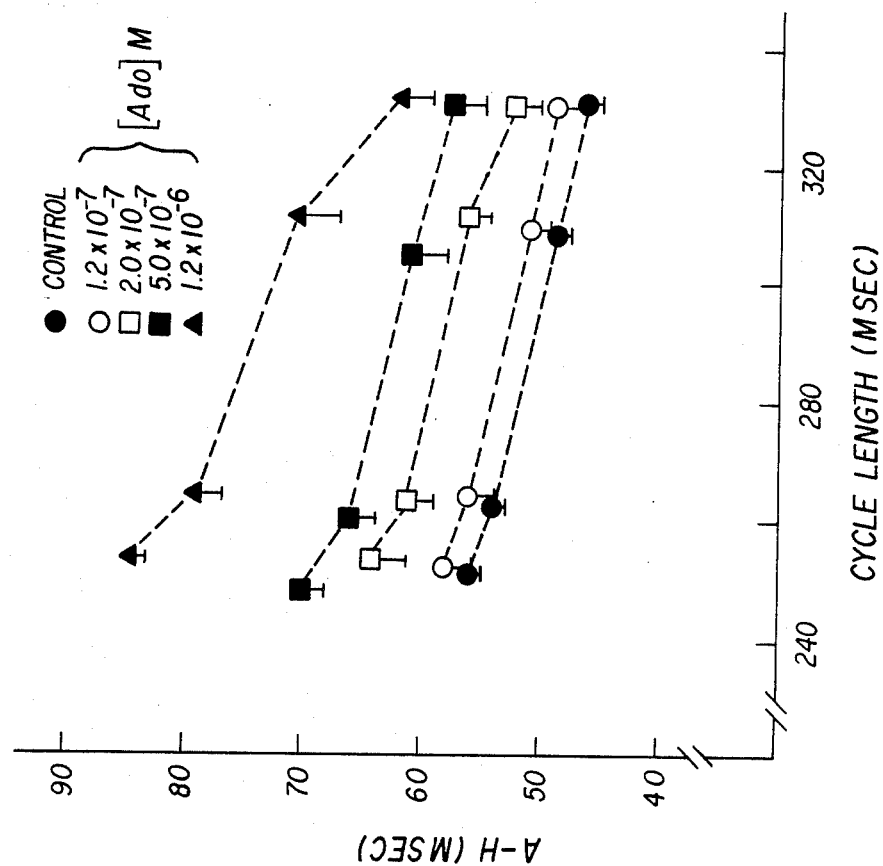

Adenosine also prolonged A-V conduction time and A-H intervals in isolated, perfused guinea pig hearts (FIG. 6). A protocol similar to that used for rabbits hearts was followed. A-H and H-V intervals, as well as A-V conduction time, were measured for each preparation. The threshold for effects in the guinea pig was lower, with $1.2 \times 10^{-7}$M adenosine causing an increase in A-V conduction time in this species ($\eta=20$) paried comparisons from five hearts, all cycle lengths, different from zero at $p<0.001$ level) compared to the statistically insignificant change of $1 \pm 1\%$ seen with $1.3 \times 10^{-7}$M adenosine in the rabbit hearts. Furthermore, the dose-response relationship appeared to be much steeper in guinea pig hearts. Adenosine at $1.2 \times 10^{-6}$ caused a $31 \pm 4\%$ ($\eta=9$ paired comparisons from four hearts, all cycle lengths) increase in A-V conduction time in this species as compared to only an $8 \pm 1\%$ increase at a similar concentration in rabbit hearts. Furthermore, adenosine at $5 \times 10^{-6}$M produced second-degree heart block in 17 of 17 trials with guinea pig hearts (cycle lengths=260-330 msec), and $1.2 \times 10^{-5}$M adenosine produced complete A-V block (A-V dissociation) in each of eight guinea pig hearts (not shown). Comparable concentrations in rabbit hearts produced only relatively mild A-V conduction delay or, at most, occasional second-degree block at high heart rates (FIG. 4).

In the guinea pig heart, as in the rabbit heart (FIG. 5), both the effects of adenosine and the conduction changes with cycle length were confined to the A-H interval (FIG. 6), whereas the H-V interval remained unaltered at 14±1 msec ($\eta$=the 7 hearts represented in FIG. 6). Conclusions about the relative threshold and dose response steepness for the two species are equally as valid for A-H inteval as for A-V conduction time although, of course, the percentage calculated are slightly higher for A-H intervals.

FIG. 2 shows an electrogram from an experiment in which $10^{-6}$M adenosine induced second-degree heart block (4:3, panel B) in a guinea pig heart. Two minutes after the initiation of an aminophylline ($10^{-5}$M) infusion (panel C), in the continued presence of adenosine, the heart block was eliminated and the A-H interval was only 16% greater than the control value (panel C vs. panel A).

This pattern was seen in eight hearts at cycle lengths between 176 and 332 msec. In other experiments, for example the one summarized in Table 1, adenosine did not cause second-degree heart block at certain cycle lengths, but only prolonged the A-H and A-V intervals. In three experiments of this type, involving several different pacing rates, $10^{-5}$M aminophylline reduced the $10^{-6}$M adenosine-induced increment in A-H interval by 65-100%. Aminophylline by itself had no significant effect on A-V conduction.

TABLE 1

Effects of Aminophylline and Atropine on the A-H Interval of Guinea Pig Hearts in the Presence of Acetylcholine, Adenosine, and MnCL$_2$

| Agonist | Cycle Length (msec) | A-H (msec) | | | |
|---|---|---|---|---|---|
| | | Control | Agonist | Agonist + aminophylline (2.5 × $10^{-5}$ M) | Agonist + atropine ($10^{-6}$ M) |
| Acetylcholine | 376 | 52 | 64 | 63 | 52 |
| (6.2 × $10^{-8}$ M) | 328 | 60 | 66 | 66 | 58 |
| | 288 | 63 | 82 | 84 | 64 |
| | 264 | 74 | 5:4 Block | 72 | |
| Adenosine | 376 | 52 | 63 | 55 | 62 |
| (1.2 × $10^{-6}$ M) | 328 | 58 | 68 | 56 | 69 |
| | 288 | 64 | 78 | 64 | 78 |
| | 264 | 72 | 5:4 Block | 74 | 5:5 Block |
| MnCl$_2$ | 376 | 48 | 70 | 74 | |
| (2 × $10^{-5}$ M) | 328 | 54 | 88 | 89 | |
| | 288 | 60 | 100 | 100 | |
| | 264 | 68 | 3.2 Block | 2.1 Block | |

Aminophylline's antagonistic action appears to be relatively specific for adenosine. Acetylcholine and manganese chloride were administered as infusions to several guinea pig heart preparations. The concentrations of these agents were adjusted to achieve A-H interval prolongation similar in magnitude to that caused by adenosine at comparable pace rates (Table 1, one experiment shown). Aminophylline (2×$10^{-5}$M) blocked or greatly attenuated the adenosine responses, as already discussed, but was without effect on the responses to acetylcholine or manganese chloride. Atropine ($10^{-6}$M), however, eliminated the effects of acetylcholine while exerting no antagonism against adenosine. Qualitatively similar effects of atropine and aminophylline on responses induced by adenosine, acetylcholine, and manganese chloride were obtained from a total of three preparations.

The results presented here confirm previous observations (Drury and Szent-Gyorgyi, J. Physiol. (Lond.), 68, pp 213-237 (1929); Stafford, Br. J. Pharmacol. Chemothery 28, pp 218-227 (1966); and Schrader et al., Pfluegers Arch, 372, pp 29-35 (1977)) that adenosine induces A-V node conduction delay and block. An additional finding is that the effects of adenosine on A-V node conduction are due to increased conduction delay between the atria and His bundle, i.e., an increased A-H interval. In contrast, the H-V interval is not affected by adenosine even at high concentrations ($10^{-4}$M). These new findings are consistent with the idea that adenosine depresses slow channel-mediated action potentials (atria and/or A-V node) whereas fast channel-mediated action potentials are not affected. (Schrader et al., J. Mol. Cell. Cardiol., 7, pp. 427-433 (1975); Belardinelli et al, Pfluegers Arch., 380, pp. 19-27 (1979)). The selectivity of adenosine's action on the A-V node is similar to that of other slow-channel blockers, such as MnCl$_2$ and verapamil (Benitez et al, Pfluegers Arch., 345, pp. 61-72 (1973); Zipes and Mendez, Circ. Res. 32, pp. 447-454 (1973). In comparison to the effects of MnCl$_2$ and verapamil (Kohlhardt et al, Pfluegers Arch., 33, pp. 115-123 (1973), however, the effects of adenosine have a rapid onset (<1 min) and can be reversed rapidly on washout.

Guinea pig hearts were more sensitive to the effects of adenosine than rabbit hearts, i.e., the threshold dose was lower and A-V block was seen more frequently in guinea pig hearts. Species differences with respect to sensitivity to the effects of adenosine on A-V node conduction have been reported previously (Drury and Szent-Gyorgyi, see above). The basis for these differences is not understood.

Temperature can modify the action of adenosine on A-V conduction. Drury and Szent-Gyorgyi noted a decreased sensitivity of the guinea pig heart (induction of A-V block) to adenosine at higher temperatures. Pilot experiments at 37° C. also showed a right-shifted adenosine dose-response curve compared to the data presented here, obtained at 34° C. The lower temperature was chosen because of the superior preparation stability it provided. Even at 37°, however, complete A-V block in the guinea pig heart with $10^{-4}$M adenosine (three experiments) was obtained. Therefore, the basic conclusion is not altered because of the use of a low temperature.

In this study the A-H interval prolongation induced by adenosine was blocked by $10^{-5}$M aminophylline, and this antagonism was specific, inasmuch as similar acetylochline- and MnCl$_2$-induced effects were not blocked by aminophylline. These findings are consistent with the notion that adenosine is competitively inhibited by theophylline (Bunger et al, Pfluegers Arch., 358, pp. 213-224 (1975)) and probably affects the A-V node conduction system by acting on the plasma membrane, as has been demonstrated for other tissues using adenosine that had been complexed to high molecular weight substances (Olsson et al, Circ. Res., 39, pp. 93-98 (1976); Schrader et al, Pfluegers Arch., 372, pp. 29-35 (1977); Hartzell, J. Physiol. (Lond.), 293, pp. 23-49 (1979)).

EXAMPLE 2

The effects of exogenous adenosine on the heart of living dogs have been demonstrated. Slowing of A-V conduction resulting from this condition has been reversed by the administration of aminophylline.

Twenty-two mongrel dogs of either sex weighing 10-18 kg were anesthetized with sodium pentobarbital (30 mg/kg intravenously). Normal saline solution was administered throughout the experiment (10 ml/kg per hour) via a catheter in the left jugular vein. Arterial blood pressure was continuously recorded on a strip-chart recorder (Gould-Brush 2200) from a catheter positioned in the aorta via the right femoral artery. Under controlled ventilation a left thoracotomy at the fourth intercostal space was performed and the heart exposed by pericardiotomy. For selective perfusion of the atrioventricular (A-V) node region the technique developed by James et al, J. Lab Clin. Med. 76;240 (1970), was used. In brief, the atrioventricular node artery (AVNA), distal branch of the left circumflex, was carefully dissected. Sutures were placed around it, but the vessel was not cannulated until control measurements were taken. The AVNA was cannulated with a small polyethylene catheter and a continuous microdrip of physiological salt solution was given to keep the catheter open.

Electrical pacing at cycle lengths ranging from 450 msec to 250 msec was applied to the atrium through teflon-coated stainless steel wires sutured to the left atrial appendage. The electrical stimulation delivered from a Grass stimulator (Model S44) via a stimulus isolation unit (SIU) as rectangular wave pulses of 2-3 msec duration and twice threshold intensity.

A His-bundle electrogram was obtained with either a standard pacing or tri-polar electrode cathether (SF) having a 1 cm interelectrode distance. The electrode catheter was introduced into the aorta via the left carotid artery and then, advanced under manual control into the ascending aorta and finally wedged in the noncoronary cusp of the aortic valve. Its position was confirmed at the end of the experiment. Extracellular electrograms from atrium and ventricule were obtained with plunge electrodes, i.e., telfon coated stainless steel wires (0.0045 inch diameter) inserted into the left atrial appendage and left ventricle with use of 25 gauge hypodermic needles. A lead-II electrocardiogram was continuously monitored and recorded at a paper speed of 50 mm/sec. His-bundle, atrial and ventricular electrograms were obtained by connecting the electrode terminals to a differential amplifier (Tektronix model 5A222N). The signals were amplified and displayed on a dual-beam oscilloscope (Tektronix model 5440). Both His-bundle and left atrial and ventricular electrograms were filtered with a low cutoff of 80 Hz and a high cutoff of 1 KH$_z$. Oscilloscope signals were displayed at sweep speeds of 10 to 50 msec/cm and photographed with a Kymographic camera (Glass model C4).

In all experiments post-mortem coronary angiograms were performed to verify the anatomy of the cannulated AVNA.

On the left atrial, ventricle and His-bundle electrograms the stimulus artifact(s), the onset of atrial (A) and ventricular (V) depolarization, and the His spike (H) were identified. These features allowed us to measure: (1) Cycle length (C.L.) as the interstimulus interval; (2) A-H interval, which represents the atrial-to-His-bundle conduction time; (3) H-V interval, which represents the His-bundle-to-ventricular conduction time; and (4) A-V interval, which represents the atrial-to-ventricular conduction time (A-VCT).

In the lead-II electrocardiogram the atrial depolarization (P wave) and ventricular depolarization (QRS) were identified. The intervals P-R or P-Q which represent the conduction time from the atrium to the ventricle were measured. All the measurements are expressed in milliseconds.

Before cannulation of the atrioventricular node artery (AVNA), control recordings were made during left atrial pacing at cycle lengths varying from 450 msec to 250 msec. At 5 minutes after cannulation of the AVNA, new control recordings at the same pacing rates were obtained. Control measurements preceded and followed all experimental interventions involving the injection of adenosine and any other drug to the AVNA. Whenever total A-V conduction time in the pre- and post-control differed by more than 10%, the intervening experimental data were discarded. Often the effects of the experimental interventions were observed at more than one cycle length.

Adenosine (Sigma) was dissolved in physiological salt solution to achieve cncentration of 10 $\mu$g, 100 $\mu$g and 100 $\mu$g per milliliter. Aliquots of 1-2 ml of these stock solutions were directly infused into the AVNA. Theophylline (Sigma) and atropine (Sigma were also prepared in physiological salt solution to achieve the desired concentrations, and then infused into the AVNA. Between all interventions the AVNA was continuously perfused with physiological salt solution to assure complete washout of the infused drugs and keep the artery open. Aminophylline (Invenex) and dipyridamole (Persantin) were administered systemically (intravenously).

Figure 7:
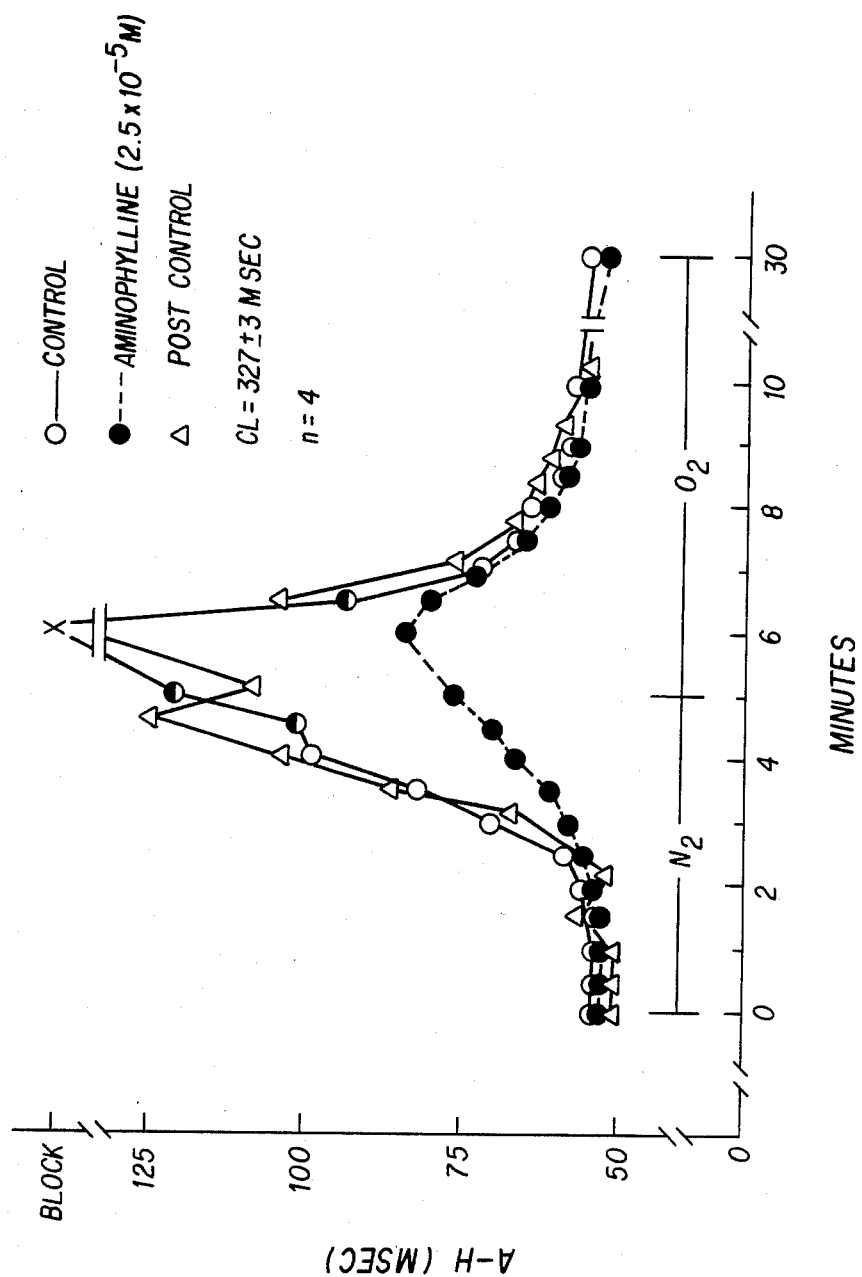
Figure 10:
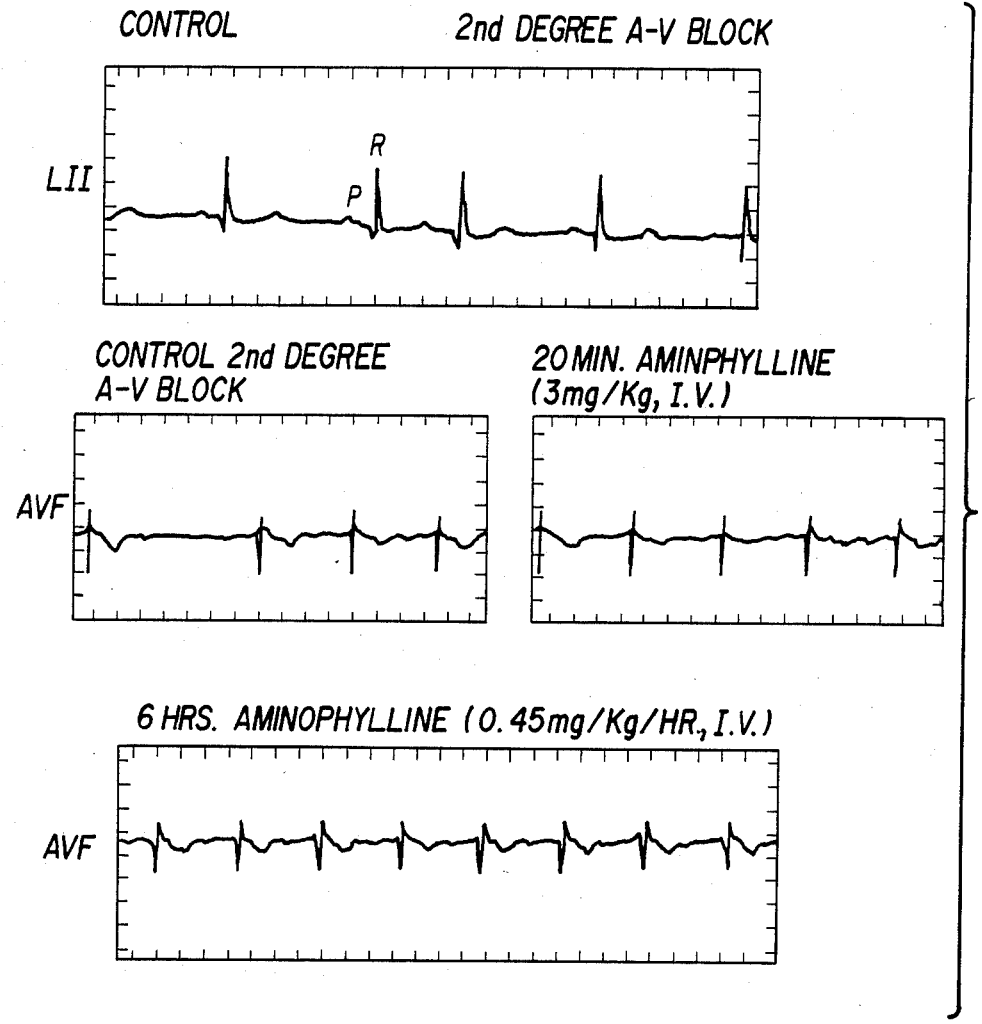
Figure 11:
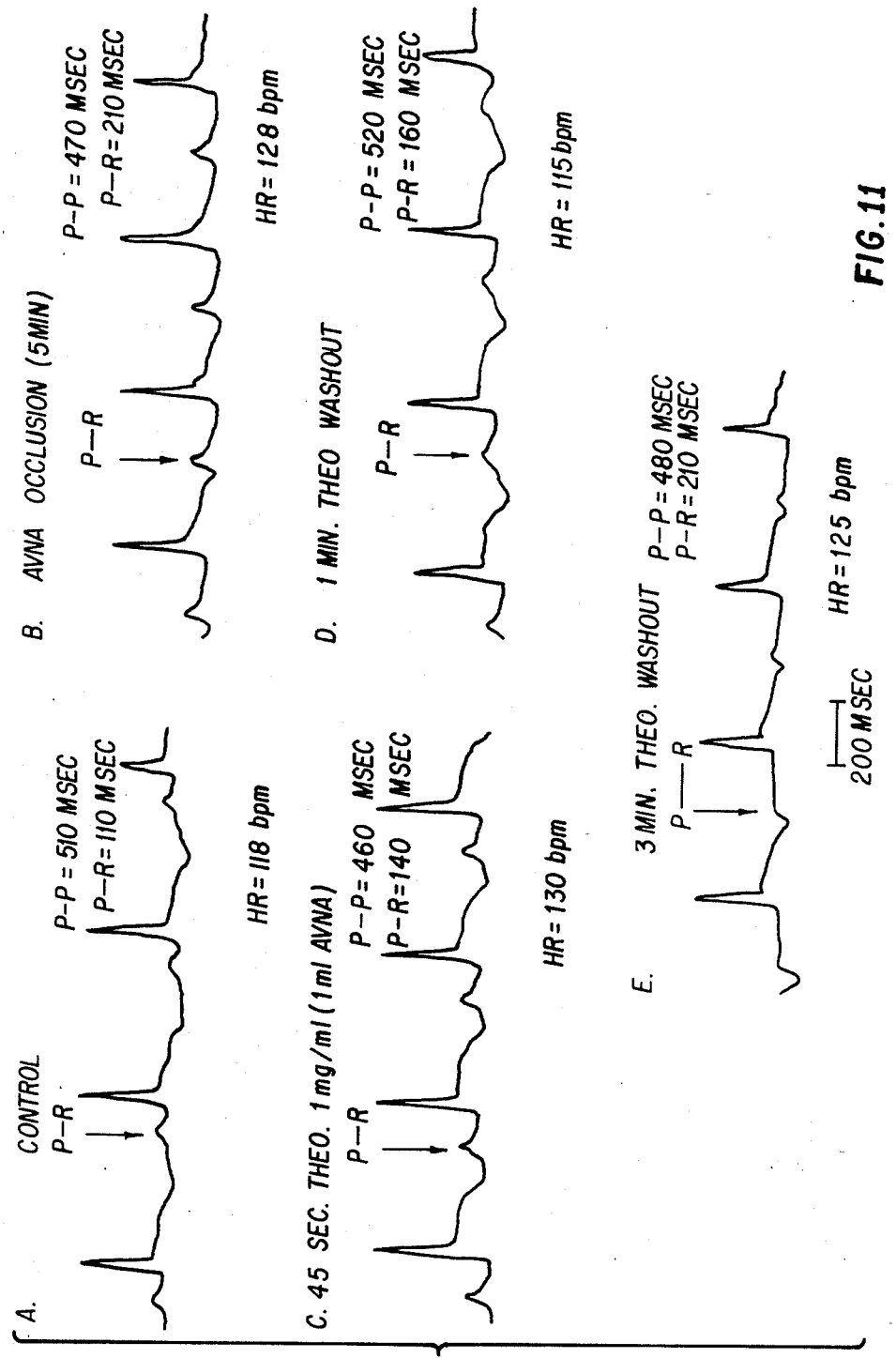

These results are summarized in a plot of A-H interval versus time during the various treatments in FIG. 7. Electrocardiograms from these procedures are shown in FIGS. 8-11.

EXAMPLE 3

Electrophysiologic studies were performed in 9 human patients in a fasting, nonsedated state after informed consent had been obtained. The group included 7 males and 2 females whose age was 53±19 yrs (mean±SD). Five of 9 patients had coronary artery disease, two had congestive cardiomyopathy and two had no known structural heart disease. Seven patients were in stable sinus rhythm and two were in chronic atrial fibrillation. All patients were undergoing electrophysiologic study as part of the management of their recurrent clinical arrhythmias. Agents known to affect adenosine metabolism (e.g., dipyridamole, diazepam) were withheld for at least 48 hours prior to study. Digoxin, if required for control of congestive heart failure (1 pt) or for control of ventricular rate in atrial fibrillation (2 pts) was continued. Three or four Fr quadripolar electrode catheters (USCI, Billerica, Mass.) with a 1 cm interelectrode distance were inserted percutaneously through femoral veins and positioned with fluoroscopic guidance in the high right atrium, the coronary sinus, (3 pts), the right ventricular apex, and across the AV junction in a position that enabled reliable recording of the His bundle potential. Intracardiac electrograms were filtered below 30 and above 500 Hz and displayed simultaneously with scalar ECG leads I, II and V on a multichannel oscilloscope (Electronics for Medicine, VR-16, Pleasantville, N.Y.). Data were stored on frequency modulated magnetic tape (Honeywell Model 101, Waltham, Mass.) and later retrieved on photographic paper at speeds of 75-200 mm/sec. Cardiac stimulation was performed with a programmable constant stimulator (Bloom Associates, Rebersburg, Pa.) that delivered rectangular pulses of 2 msec duration at 4 times diastolic threshold. The following protocol was used: (1) During the patient's endogenous rhythm, intravenous boluses of adenosine were injected through a femoral vein cannula beginning with 0.0375 mg/kg and increasing in 0.0375 mg/kg increments until an effect upon sinus rate or AV conduction was noted. (2) Once the dose required to produce electrophysiologic effects was acheived and its effect confirmed during a second injection, repeated sequential boluses at that dose were injected during atrial pacing, atrioventricular pacing, ventricular pacing, and in one patient during stimulation-induced ventricular tachycardia.

Systemic blood pressure was monitored using a intra-arterial cannula placed in either a radial or femoral artery.

Adenosine was obtained from Sigma Chemical Company (St. Louis, Mo.) and was suspended in normal saline at a concentration of 10 mg/ml. The solution was prepared under sterile conditions and assayed by high pressure liquid chromatography. The solution contained greater than 95% pure adenosine with small amounts of contamination by its breakdown products, inosine and hypoxanthine.

Figure 12:
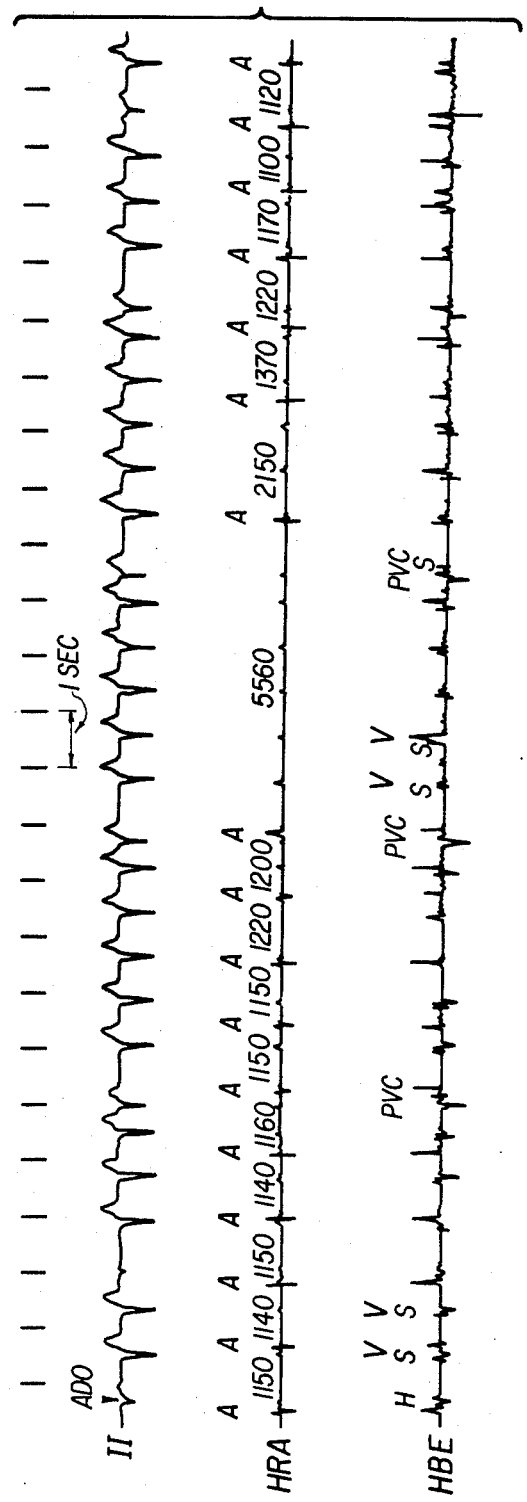

Adenosine injection produced a transient slowing of atrial rate in all 7 patients who were initially in sinus rhythm. The mean dose required to produce this effect was $0.2 \pm 0.11$ mg/kg. This effect was isolated by fixed rate ventricular pacing in 4 patients in whom ventriculoatrial conduction was not present. In these patients, adenosine injection produced atrial slowing leading to a brief (<10 seconds) period of atrial arrest (FIG. 12). This Figure shows the effect of adenosine on atrial activity in sinus rhythm. From top to bottom the tracing represents time lines, surface electrocardiographic lead II and intracardiac recordings from the right atrium (RA) and the bundle of His (HBE). The recording was made during ventricular pacing at 600 msec. AV dissociation and occasional PVC's may be observed. At the arrow, adenosine (ADO) 0.075 mg/kg was injected. Several seconds later atrial arrest was observed with gradual return to the original atrial cycle length.

Figure 13:
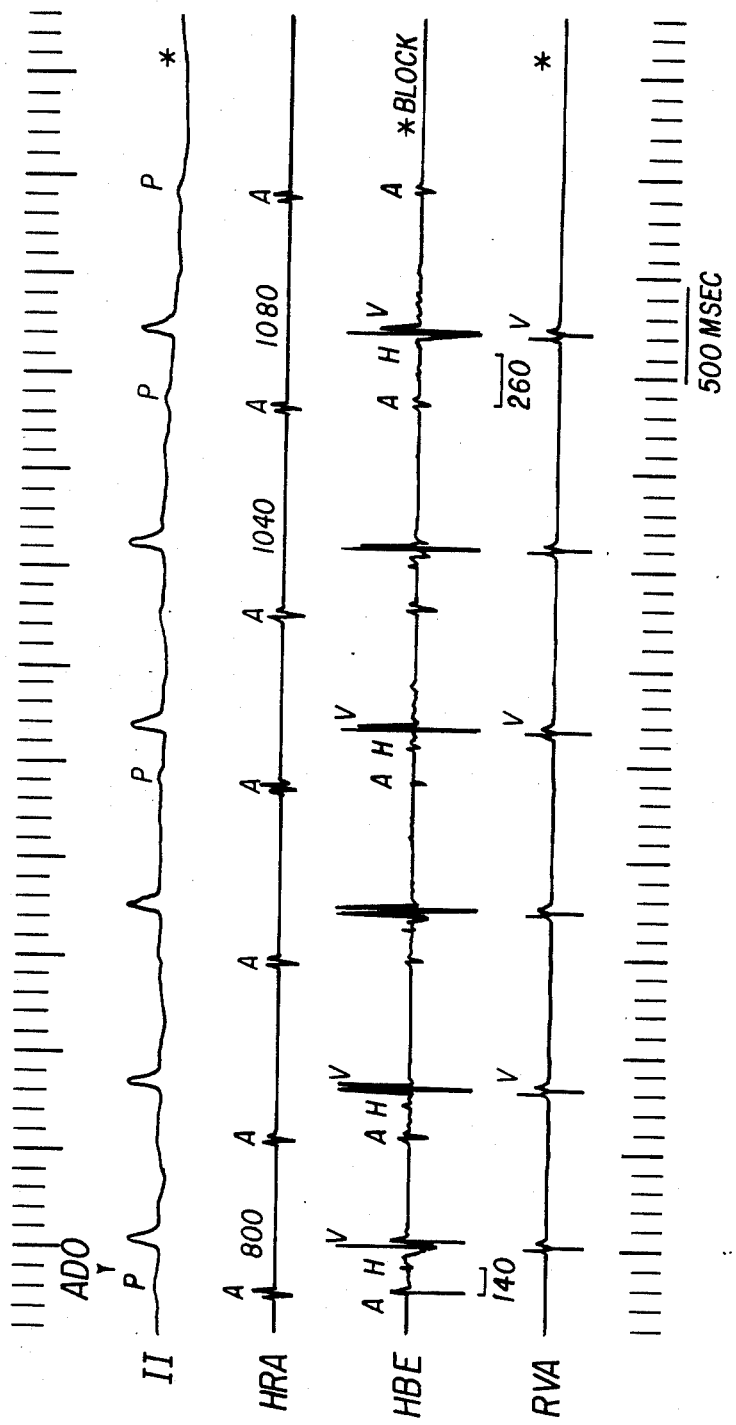

Furthermore, adenosine produced transient (<10 seconds) high grade atrioventricular block when it was injected during sinus rhythm, atrial fibrillation or atrial pacing. If the effects on atrial rate were controlled by atrial pacing, the effect observed was a prolongation of the AH interval until block above the bundle of His was observed (FIG. 13). This Figure shows the effect of adenosine on the AV node. The tracings in each panel represent from top to bottom time lines, surface electrocardiographic lead II, and intracardiac recordings from the high right atrium (HRA), the bundle of His (HBE) and the right ventricular apex (RVA). The tracing in the bottom panel was obtained 2 seconds after the end of the top tracing. During atrial pacing at a cycle length of 880 msec, adenosine, 0.225 mg/kg is injected at the arrow. Over the next several seconds, the AH interval was prolonged from 110 msec to 200 msec and then returned, in the bottom panel, to its initial value. The HV interval of the conducted beats remained unchanged. Ventriculoatrial conduction during ventricular pacing was also blocked. The dose required to produce transient Av block was similar to that shown to produce an effect during sinus rhythm ($0.16 \pm 0.1$ mg/kg). The difference in means reflects a slightly greater sensitivity in the two patients with atrial fibrillation as their baseline rhythm.

The effect of adenosine in a patient with Wolff-Parkinson-White syndrome is shown in FIG. 14. This Figure shows the effect of adenosine in a patient with preexcitation. In panels A and B the tracings represent surface electrocardiographic lead II and His bundle electrogram. Adenosine 0.185 mg/kg was injected during atrial pacing at a cycle length of 700 msec just before the start of panel A. The QRS complex gradually becomes more preexcited and the His potential became lost in the ventricular electrogram. Several seconds later (Panel B), the QRS morphology returned to baseline and the H spike returned to its original position. The PR interval remained unchanged throughout. In Panel C, electrocardiographic lead II and radial arterial pressure during this period are shown. No change is seen in systolic blood pressure despite the marked change in AV conduction. Adenosine increased the degree of preexcitation as AV nodal block was produced. In this patient, as well as in other patients, if atrioventricular or ventricular pacing was used, no effect on systemic arterial pressure was observed (Panel C). In one patient, administration of adenosine during ventricular tachycardia initiated earlier by programmed ventricular stimulation, i.e., a tachycardia which does not result from re-entry in the AV node, blocked AV conduction but did not modify or terminate the tachycardia (not shown).

Atropine, 0.15 mg/kg I.V. was administered to 3 patients and adenosine administration was repeated. In none of these patients was an attenuation of adenosine effect observed.

Several patients reported a heavy feeling in their chest after injection of adenosine during sinus rhythm but this was eliminated if ventricular pacing was used to provide a minimum ventricular rate and a constant systemic arterial pressure.

EXAMPLE 4

An experiment was conducted to test whether or not ATP and its less hydrolyzable analog $\beta,\gamma$-methylene-ATP also cause A-V block and prolonged the A-H interval. Isolated guinea-pig hearts (n=9) were perfused at a constant flow (4-5 ml/min per g) with Krebs-Henseleit solution gassed with 95% $O_2$+5% $CO_2$ (35° C., pH 7.4). Extracellular electrograms were recorded from left atrium, His bundle and left ventricle. The overall control (pre- and post-intervention) for A-H (msec) was $32.6 \pm 1.0$ msec ($\overline{X} \pm$ sem).

| | A-H Prolongation (msec) | | |
|---|---|---|---|
| Concentration (M) | ATP Analog | ATP | ADO |
| $7 \times 10^{-6}$ M | 4 | 8 | 27 |
| $2 \times 10^{-5}$ M | 7 | 20 | A-V block |

In three out of eight hearts $2\times10^{-5}$M ATP caused second-degree A-V block. ADO ($7\times10^{-6}$M) caused second degree A-V block in two out of seven hearts and complete A-V block in all hearts at $2\times10^{-5}$M.

In addition the effects of ATP were markedly potentiated by nitrobenzylthioinosine, a nucleoside transport blocker. Conversely, aminophylline, a competitive antagonist of ADO-induced A-H prolongation, antagonized the ATP-induced A-H prolongation. In summary, these data show that in contrast to ATP, the $\beta,\gamma$-methylene ATP which is more resistant to hydrolysis than ATP has essentially no effect on the A-V transmission. Thus, it is reasonable to suggest that ATP-induced prolongation of A-H interval and A-V block is a consequence of its degradation to ADO.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of treating supraventricular tachycardia caused by re-entry in the AV node, comprising the steps of:
   (a) administering intravenously to a human afflicted with the tachycardia, 0.01–0.25 mg/kg of body weight of adenosine sufficient to restore normal rhythm.

2. The method of claim 1, wherein said tachycardia is Wolff-Parkinson-White syndrome.

3. The method of claim 1, wherein said tachycardia is reciprocating junctional tachycardia.

4. The method of claim 1, wherein said amount is 1–8 mg.

5. The method of claim 1, wherein said amount is about 0.06 mg/kg.

6. A method of diagnosing supraventricular tachycardia caused by re-entry in the AV node, comprising the steps of:
   (a) administering intravenously to a human afflicated with the tachycardia 0.01–0.25 mg/kg of body weight of adenosine;
   (b) monitoring the heart beat of said human for restoration of normal sinus rhythm; and
   (c) determining the existence of the tachycardia.

7. The method of claim 6, wherein said tachycardia is Wolff-Parkinson-White syndrome.

8. The method of claim 6, wherein said tachycardia is reciprocating junctional tachycardia.

9. The method of claim 6, wherein said amount is 1–8 mg.

10. The method of claim 6, wherein said amount is about 0.06 mg/kg.

* * * * *

UNITED STATES PATENT AND TRADEMARK OFFICE
CERTIFICATE OF CORRECTION

PATENT NO.  : 4,673,563
DATED       : June 16, 1987
INVENTOR(S) : Robert M. Berne et al.

It is certified that error appears in the above-identified patent and that said Letters Patent is hereby corrected as shown below:

Column 1,
After the title insert the following paragraph:

-- U.S. Government Rights
This invention was made with United States Government support under Grant No. HL 10384, awarded by the National Institutes of Health. The United States Government has certain rights in the invention. --

Signed and Sealed this

Second Day of July, 2002

Attest:

Attesting Officer

JAMES E. ROGAN
Director of the United States Patent and Trademark Office